Figure 1:
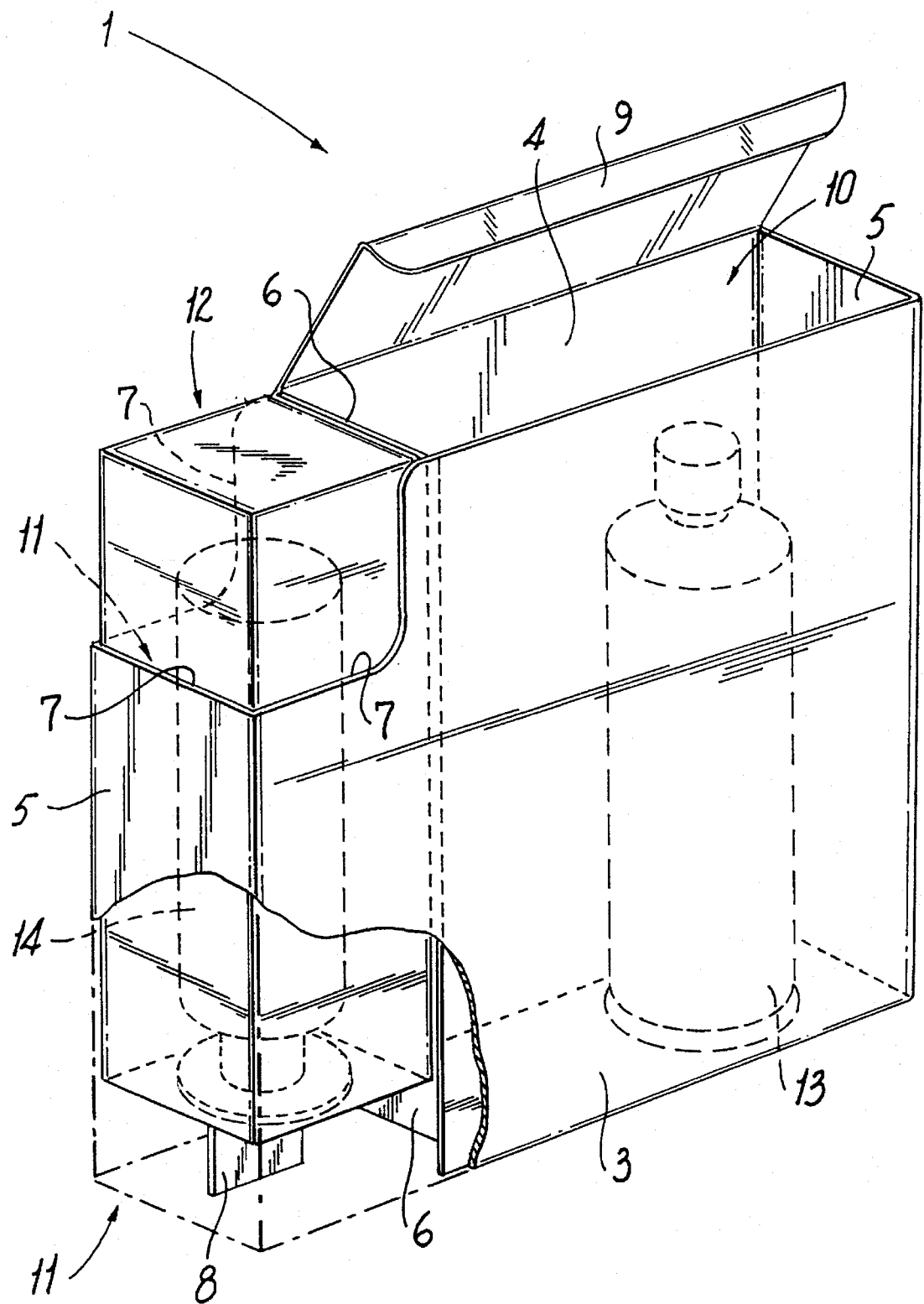

United States Patent [19]

Rohrbough et al.

[11] Patent Number: 5,609,248

[45] Date of Patent: Mar. 11, 1997

[54] MULTI-PART PACKAGE

[75] Inventors: John Rohrbough, Scottsdale, Ariz.;
John Franck, City of Industry, Calif.

[73] Assignee: F. H. Faulding & Co. Limited,
Parkside, Australia

[21] Appl. No.: 450,470

[22] Filed: Apr. 20, 1995

Related U.S. Application Data

[63] Continuation of PCT/AU93/00542, Oct. 21, 1993, published as WO94/08857, Apr. 28, 1994.

[30]   Foreign Application Priority Data

Oct. 21, 1992 [AU] Australia ................................. PL5393

[51] Int. Cl.⁶ .................................................. B65D 71/12
[52] U.S. Cl. ..................... 206/216; 206/570; 229/120.18; 220/23.83
[58] Field of Search .................................. 220/23.83, 500, 220/505, 525, 523, 528, 553, 557; 229/120.02, 120.08, 120.11, 120.18, 120.37, 23 R; 206/570, 571, 528, 85, 86, 87, 90, 94, 95, 216

[56]                 References Cited

U.S. PATENT DOCUMENTS

| | | |
|---|---|---|
| 1,556,514 | 10/1925 | Feldman .......................... 229/120.18 X |
| 2,015,278 | 9/1935 | Meyer . |
| 2,060,513 | 11/1936 | Marx . |
| 3,111,253 | 11/1963 | Hennessey . |
| 3,563,449 | 2/1971 | Forbes . |
| 3,567,105 | 3/1971 | McFarlin . |
| 3,627,117 | 12/1971 | Giesler . |
| 3,866,747 | 2/1975 | Scholz . |
| 4,170,295 | 10/1979 | Kuehl . |
| 4,252,237 | 2/1981 | Baclit ...................................... 206/86 |
| 4,407,442 | 10/1983 | Watson . |

FOREIGN PATENT DOCUMENTS

| | | |
|---|---|---|
| 30530/30 | 10/1931 | Australia . |
| 16212/34 | 2/1935 | Australia . |
| 3917/54 | 12/1955 | Australia . |
| 46314/59 | 8/1959 | Australia . |
| 55918/59 | 6/1960 | Australia . |
| 10227/76 | 7/1977 | Australia . |
| 73155/81 | 2/1982 | Australia . |
| 36325/84 | 6/1985 | Australia . |
| 64938/86 | 5/1988 | Australia . |
| 68537/90 | 7/1991 | Australia . |
| 83406/91 | 3/1992 | Australia . |
| 0170637 | 2/1986 | European Pat. Off. . |
| 0171333 | 2/1986 | European Pat. Off. . |
| 2050009 | 3/1971 | France . |
| 2184067 | 12/1973 | France . |
| 2602497 | 2/1988 | France . |
| 3229544 | 10/1983 | Germany . |
| 2199727 | 7/1988 | United Kingdom . |
| WO91/17099 | 11/1991 | WIPO . |

*Primary Examiner*—Jacob K. Ackun
*Attorney, Agent, or Firm*—Darby & Darby

[57]                   ABSTRACT

A package is disclosed that enables packaging of associated items in a single pack. Typical of the items to be packaged are pharmaceutical drugs and associated drug delivery apparatus. The package (1) includes a main container or first compartment (10) adapted to contain a first one of the items e.g. drug delivery apparatus and a support or second compartment (11) adapted to releasably hold a subsidiary container to contain the second of the items e.g. vial or similar container. The subsidiary container may take the form of a sleeve or box retained with the second compartment.

21 Claims, 1 Drawing Sheet

MULTI-PART PACKAGE

This is a continuation of international application Ser. No. PCT/AU93/00542, filed Oct. 21, 1993 published as WO94/08857 filed Apr. 28, 1994.

This invention relates to packaging in general, and in particular to a multi-part package.

This package is applicable for the packaging of pharmaceutical drugs together with an associated drug delivery apparatus and it will be convenient to hereinafter disclose the invention in relation to that exemplary application. It is to be appreciated, however, that the invention is not limited to that application.

Pharmaceutical drugs such as narcotics are usually stored within containers such as shell glass vials and must be administered using a drug delivery apparatus such as a hypodermic syringe or other injector device. It is therefore generally necessary to have a separate drug delivery apparatus for each drug containing vial.

It would be advantageous to package a drug delivery apparatus together with each vial. However drugs such as narcotics should be stored within a vault or a refrigerator. Because of space limitations within the vault/refrigerator, it is preferable that only the vials be stored therein with the drug delivery apparatus being stored separately.

It is therefore an object of the present invention to overcome, or at least alleviate, one or more of the difficulties or deficiencies of the prior art.

Accordingly, in a first aspect of the present invention, there is provided a multi-part package including a main container;

at least one subsidiary container removably connected to the main container; and a support means for supporting the subsidiary container in juxtaposition with the main container.

This invention is described herein with reference to the package in a normal use orientation, and terms such as "top" and "bottom" should be construed in the light of this orientation. However, it is to be appreciated that other orientations may be equally possible and that consequential changes in terms such as those above may be required in the light of those other orientations for a proper and complete understanding of the invention.

The dimensions of the main container and subsidiary container may be governed by the applications to which they are to be applied.

The main container may be dimensioned to accommodate a drug delivery apparatus such as an injector device. The subsidiary container may be dimensioned to accommodate drug vial container such as a shell glass vial.

Alternatively the main container is dimensioned to accommodate a vial container including a solvent for the freeze dried or powder drug.

In a further alternative embodiment the main container and subsidiary container may be dimensioned to receive containers including two preparations which may be unstable if mixed together. Where applicable, each preparation may be stored at the correct temperature for each (for example one may be refrigerated; the other may be maintained at room temperature).

This invention will be hereinafter described with reference to only one subsidiary container although more than one subsidiary container may be provided.

In a preferred embodiment of the multi-part package of the present invention, the main container may be in the form of a box. The main container may be manufactured in any suitable manner and from any suitable material. The main container may be manufactured from sheet material such as cardboard or plastic material.

The main container may be provided in the form of a container blank. The container blank may be subsequently folded or glued to form the main container. The main container may include front and rear panels joined together at opposing sides thereof by side panels to form a four-sided sleeve. The sleeve may have a rectangular or square cross-section and may have openings at each end thereof.

The main container may include closure means provided to cover the opening at the bottom end thereof. The bottom end of the sleeve may for example be provided with a closure or tuck flap with cooperating tabs which fold over the opening and co-operate to provide a closure means of the type well known in packaging technology. It is to be appreciated that other closure means are also envisaged. For example, a separate closure cap may be provided to cover the bottom opening of the injector container sleeve.

The main container may include a separation panel joined to and extending between the front and rear panels.

The separation panel may extend parallel to the side panels so as to separate the main container into a first and second compartment. The first compartment, referred to below as the storage compartment, may be adapted to accommodate a drug delivery apparatus. The top end may be closed by closure means such as a tuck, flap to provide the storage space for the drug delivery apparatus. The second compartment, referred to below as the holding compartment, may provide the support means for supporting the subsidiary container. The second compartment may have an open top end.

The subsidiary container of the multi-part package, for accommodating the drug vial container may be of similar manufacture and materials to the main container. The subsidiary container may be provided in the form of a container blank.

The subsidiary container may also be in the form of an elongate box having opposing front and rear panels and adjoining side panels to provide a four-sided sleeve. The sleeve may have a rectangular or square cross-section and the open ends of the sleeve may be closed off by closure means to provide the dosage container storage space therein. Tuck flaps may for example be provided at the top and bottom ends of the sleeve to provide a box in a form commonly used for packaging. Other configurations for the subsidiary container are also envisaged. For example, the container may be in the form of a tube having a circular cross-section.

In use, the subsidiary container may be inserted into the second or holding compartment of the main container through its open end to form the multi-part package. The subsidiary container may be dimensioned such that it fits securely within the holding compartment, there being frictional engagement between the walls of the subsidiary container and the holding compartment.

To facilitate removal and reinsertion of the subsidary container, sections of the panels at the top end of the holding compartment of the main container may be removed to allow a portion of the sides of the subsidiary container to remain exposed when accommodated within the holding compartment. This exposed portion may be gripped to facilitate removal of the subsidiary container therefrom. Preferably, a portion of the front and rear panels and adjoining side panel adjacent the open end of the holding compartment may be removed.

The top of the subsidiary container, when fully accommodated within the holding compartment, may be level with the top of the main container. This makes it easier to grip the vial container as well as providing an aesthetically pleasing appearance to the assembled package.

If the subsidiary container is shorter in length than the main container, the second or holding compartment of the main container may further include an abutment at the bottom end thereof.

The abutment may be dimensioned to support the subsidiary container at the desired level within the multi-part package. This abutment may for example be provided by a tongue extending from the bottom end of the separation panel of the main container into the second or holding compartment. The subsidiary container may sit on said tongue when supported within the holding compartment.

In a preferred form, the main and subsidiary containers of the multi-part package may come in different sizes so that only matching container pairs may fit together properly. This may assist in ensuring that the correct drug is rematched with the correct drug delivery apparatus. The respective containers may also be colour matched for identification.

It will be understood that as well as allowing the drug vial container to be separately stored, the subsidiary containers also provide additional protection from breakage during shipment. This is important for example where shell glass vials are used as the drug vial container. Furthermore, because the vial itself may not be tamper evident, the subsidiary container may be sealed to afford tamper evident assurance.

The multi-part package of the present invention accordingly provides separate subsidiary and main containers for respectively containing a drug vial container and its associated drug delivery apparatus. The separate containment of the drug vial container and drug delivery apparatus afford additional protection from breakage during transport thereof. Furthermore, the subsidiary container containing the drug may be separated from the main container thereby allowing the drug to be stored separately from the drug delivery apparatus. This is important when the drugs must be stored in a vault or refrigerator for security, safety or stability purposes and there are space limitations therein. The drug container may be removed and stored within the vault or refrigerator with the drug delivery apparatus being stored separately. The drug container may be subsequently reconnected to the main container.

The present invention will now be more fully described with reference to the accompanying drawings. It should be understood, however, that the description following is illustrative only and should not be taken as a restriction on the generality of the invention described above.

In the drawings:

FIG. 1 is a perspective view of an example embodiment of the multi-part package of the present invention;

In more detail, FIG. 1 illustrates an embodiment of the multi-part package where the main or injector container 1 is in the form of a box having a front panel 3 and rear panel 4 and adjoining side panels 5. A separation panel 6 separates the main container 1 into a first or storage compartment 10 for accommodating a drug delivery apparatus 13 and a second or holding compartment 11. A tuck flap 9 is used to close the top opening of the storage compartment 10. A similar tuck flap (not shown) is provided at the bottom to close off the bottom openings of both the storage and holding compartments 10, 11.

The subsidiary container 12 for accommodating a drug vial container 14 is also in the form of a box which may be accommodated within the holding compartment 11. A cutaway section 7 is provided in the front and rear panels 3, 4 and the side wall 5 at the top end of the holding compartment 11. A tongue 8 extends from the separation panel 6 at the bottom end of the holding compartment 11. The drug vial container sits on the tongue 8 so that its top is level with the top of the injector container 1 with a portion of the drug vial container remaining exposed to facilitate removal therefrom.

Finally, it is to be understood that various modifications and/or alterations may be made to the package without departing from the ambit of the present invention as described herein.

We claim:

1. A multi-part package for packaging a drug vial container containing a drug and a drug delivery apparatus, or for packaging a drug container containing a freeze dried or powder drug, and a vial container containing solvent for the freeze dried or powder drug, said multi-part package including:

a main container dimensioned to accommodate the drug delivery apparatus or the vial container, respectively, said main container being in the form of a box having front and rear panels joined together at opposing edges thereof by respective side panels, a separation panel extending between and joined to the front and rear panels so as to separate the main container into first and second storage compartments, each of the storage compartments being defined by the front and rear panels, the separation panel and a respective side panel, and the panels together defining open top and bottom ends to each of the storage compartments, bottom closure means joined to at least one of the panels adjacent the bottom end and covering so as to close the bottom end of both storage compartments, top closure means joined adjacent the top end to at least one of the panels and covering so as to close the top end of the first storage compartment but not covering the top end of the second storage compartment, the top closure means being actuable to uncover the top end of the first storage compartment for access thereto, and the open top end of the second storage compartment remaining permanently uncovered for access thereto; and at least one subsidiary container dimensioned to accommodate the drug vial container or the drug container, respectively said subsidiary container being removably carried in the second storage compartment and being removable from and insertable into the second storage compartment without actuating the top closure means and while the top closure means closes the first storage compartment.

2. A multi-part package according to claim 1, wherein the subsidiary container is in the form of a box having front and rear panels and adjoining side panels, the subsidiary container being dimensioned so as to nest in the second storage compartment such that there is face-to-face frictional engagement between respectively panels of the subsidiary container and the main container.

3. A multi-part package according to claim 2, wherein the subsidiary container is at lest substantially the same length as the main container so when nested in the second compartment, a top end thereof is at least substantially level with the top end of the first storage compartment.

4. A multi-part package according to claim 2 wherein the subsidiary container is shorter in length than the main container, and the main container further includes an abutment in the second storage compartment toward the bottom end thereof dimensioned to support the subsidiary container at a desired height within the second storage compartment relative to the main container.

5. A multi-part package according to claim 4, wherein the abutment includes tongue extending from the separation panel into the second storage compartment and on which the subsidiary container bears for support.

6. A multi-part package according to claim 2, wherein a section of at least one of the panels defining the second storage compartment is removed adjacent the open top end thereof so that a corresponding panel portion of the subsidiary container remains exposed when carried within the second storage compartment.

7. A multi-part package according to claim 6, wherein sections of the front, rear and one side panel defining the second compartment are removed so as to expose corresponding panel portions of the subsidiary container when carried in the second storage compartment.

8. A multi-part package according to claim 1, wherein the top closure means includes a cover flap foldably joined to the rear panel and configured for folding so as to overlie the top end of the first storage compartment, and a tuck flap foldably joined to the cover flap for inserting into the first storage compartment behind the front panel to hold the cover flap in position overlying the top end and thereby close the top end of the first storage compartment.

9. A multi-part package according to claim 1, wherein the main container is constructed in one piece from a pre-formed blank of sheet material folded and joined into the box form.

10. A multi-part package according to claim 1, wherein the subsidiary container is constructed in one piece from a pre-formed blank of sheet material folded and joined into a box form.

11. A method for packaging a drug vial container containing a drug, and a drug delivery apparatus, or for packaging a drug container containing a freeze dried or powder drug, and a vial container containing solvent for the freeze dried or powder drug, said method including providing a main container in the form of a box having front and rear panels joined together at opposing edges thereof by respective side panels, a separation panel extending between and joined to the front and rear panels so as to separate the main container into first and second storage compartments, each of the storage compartments being defined by the front and rear panels, the separation panel and a respective side panel, and the panels together defining open top and bottom ends to each of the storage compartments, bottom closure means joined to at least one of the panels adjacent the bottom end and covering so as to close the bottom end of both storage compartments, top closure means joined adjacent the top end to at least one of the panels and covering so as to close the top end of the first storage compartment but not covering the top end of the second storage compartment, the top closure means being actuable to uncover the top end of the first storage compartment for access thereto, and the open top end of the second storage compartment remaining permanently uncovered for access thereto providing at least one subsidiary container removably carriable in the second storage compartment; the subsidiary container being removable from and insertable into the second storage compartment without actuating the top closure means and while the top closure means closes the first storage compartment, thereby enabling separate storage of the main container and the subsidiary container; accommodating the drug delivery apparatus or the vial container, respectively, in the first storage compartment of the main container;

accommodating the drug vial container or the drug container, respectively, in the subsidiary container; and when required, separately storing the main container and the subsidiary container; and following storage, inserting the subsidiary container into the second storage compartment to form a multi-part package containing the drug delivery apparatus and the drug vial container, or containing the vial container and drug container, respectively.

12. A method according to claim 11, wherein the subsidiary container is in the form of a box having front and rear panels and adjoining side panels, the subsidiary container being dimensioned so as to nest in the second storage compartment such that there is face-to-face frictional engagement between respectively panels of the subsidiary container and the main container.

13. A method according to claim 12, wherein the subsidiary container is at lest substantially the same length as the main container so, when nested in the second compartment, a top end thereof is at least substantially level with the top end of the first storage compartment.

14. A method according to claim 12, wherein the subsidiary container is shorter in length than the main container, and the main container further includes an abutment in the second storage compartment toward the bottom end thereof dimensioned to support the subsidiary container at a desired height within the second storage compartment relative to the main container.

15. A method according to claim 14, wherein the abutment includes tongue extending from the separation panel into the second storage compartment and on which the subsidiary container bears for support.

16. A method according to claim 12, wherein a section of at least one of the panels defining the second storage compartment is removed adjacent the open top end thereof so that a corresponding panel portion of the subsidiary container remains exposed when carried within the second storage compartment.

17. A method according to claim 16, wherein sections of the front, rear and one side panel defining the second compartment are removed so as to expose corresponding panel portions of the subsidiary container when carried in the second storage compartment.

18. A method according to claim 11, wherein the top closure means includes a cover flap foldably joined to the rear panel and configured for folding so as to overlie the top end of the first storage compartment, and a tuck flap foldably joined to the cover flap for inserting into the first storage compartment behind the front panel to hold the cover flap in position overlying the top end and thereby close the top end of the first storage compartment.

19. A method according to claim 11, wherein the main container is constructed in one piece from a pre-formed blank of sheet material folded and joined into the box form.

20. A method according to claim 11, wherein the subsidiary container is constructed in one piece from a pre-formed blank of sheet material folded and joined into a box form.

21. A method of use of a multi-part package containing a drug vial container containing a drug, and a drug delivery apparatus, or containing a drug container containing a freeze dried or powder drug, and a vial container containing solvent for the freeze dried or powder drug, said multi-part package including:

a main container accommodating the drug delivery apparatus or the vial container, respectively, said main container being in the form of a box having
front and rear panels joined together at opposing edges thereof by respective side panels,
a separation panel extending between and joined to the front and rear panels so as to separate the main container into first and second storage compartments, each of the storage compartments being defined by the front and rear panels, the separation panel and a respective side panel, and the panels together defining open top and bottom ends to each of the storage compartments,
bottom closure means joined to at least one of the panels adjacent the bottom end and covering so as to close the bottom end of both storage compartments,
top closure means joined adjacent the top end to at least one of the panels and covering so as to close the top end of the first storage compartment but not covering the top end of the second storage compartment, the top closure means being actuable to uncover the top end of the first storage compartment for access thereto, and the open top end of the second storage compartment remaining permanently uncovered for access thereto; and at least one subsidiary container accommodating the drug vial container or the drug container, respectively, said subsidiary container being removably carried in the second storage compartment and being removable from and insertable into the second storage compartment without actuating the top closure means and while the top closure means closes the first storage compartment;

said method including
separately storing the main container and the subsidiary container; and
following storage, inserting the subsidiary container into the second storage compartment to reform the multi-part package containing the drug delivery apparatus and the drug vial container, or containing the vial container and drug container, respectively.

* * * * *